(12) United States Patent
Seufert

(10) Patent No.: US 6,880,977 B2
(45) Date of Patent: Apr. 19, 2005

(54) ANTI-FRICTION BEARING FOR A MAGNETIC RESONANCE TOMOGRAPHY APPARATUS

(75) Inventor: Matthias Seufert, Oberreichenbach (DE)

(73) Assignee: Siemens Aktiengesellschaft, Münich (DE)

( * ) Notice: Subject to any disclaimer, the term of this patent is extended or adjusted under 35 U.S.C. 154(b) by 94 days.

(21) Appl. No.: 10/343,506
(22) PCT Filed: Sep. 17, 2001
(86) PCT No.: PCT/DE01/03583
§ 371 (c)(1), (2), (4) Date: Jan. 31, 2003
(87) PCT Pub. No.: WO02/27203
PCT Pub. Date: Apr. 4, 2002

(65) Prior Publication Data
US 2003/0156770 A1 Aug. 21, 2003

(30) Foreign Application Priority Data
Sep. 28, 2000 (DE) .......................... 100 48 192

(51) Int. Cl.⁷ .............................. F16C 19/50
(52) U.S. Cl. ........................................ 384/446
(58) Field of Search ................. 384/58, 446, 449, 384/492, 476

(56) References Cited

U.S. PATENT DOCUMENTS

| 2,992,868 A | | 7/1961 | Vacha |
| 5,150,398 A | | 9/1992 | Nishioka et al. |
| 5,302,030 A | * | 4/1994 | Buie et al. .................. 384/449 |
| 5,439,297 A | | 8/1995 | Kitayama |
| 5,961,222 A | * | 10/1999 | Yabe et al. ................. 384/476 |
| 6,030,128 A | * | 2/2000 | Pontzer ...................... 384/476 |

FOREIGN PATENT DOCUMENTS

| DE | 1 892 000 | 4/1964 |
| EP | 0 562 865 | 9/1993 |
| WO | WO 98/46983 | 11/1998 |

OTHER PUBLICATIONS

Patent Abstracts of Japan Publication No. 10037949 for Japanese Application No. 08209331.
Technische Produktinfromation TPI 41 (Amagnetische, gehärtete Wälzlager) of INA Wälzlager Schaeffler KG, Apr. 1995.
Hauptkatalog 94/96 (Räder, Rollen, Technische Teile) of Räder–und Rollenfabrik Räder–vogel (p. 40).

* cited by examiner

Primary Examiner—Thomas R. Hannon
(74) Attorney, Agent, or Firm—Schiff Hardin LLP

(57) ABSTRACT

An antifriction bearing for a magnetic resonance tomography apparatus has magnetic rolling members and an inner ring and an outer ring between which the rolling members roll. The outer ring is surrounded by a nonmagnetic ring.

16 Claims, 1 Drawing Sheet

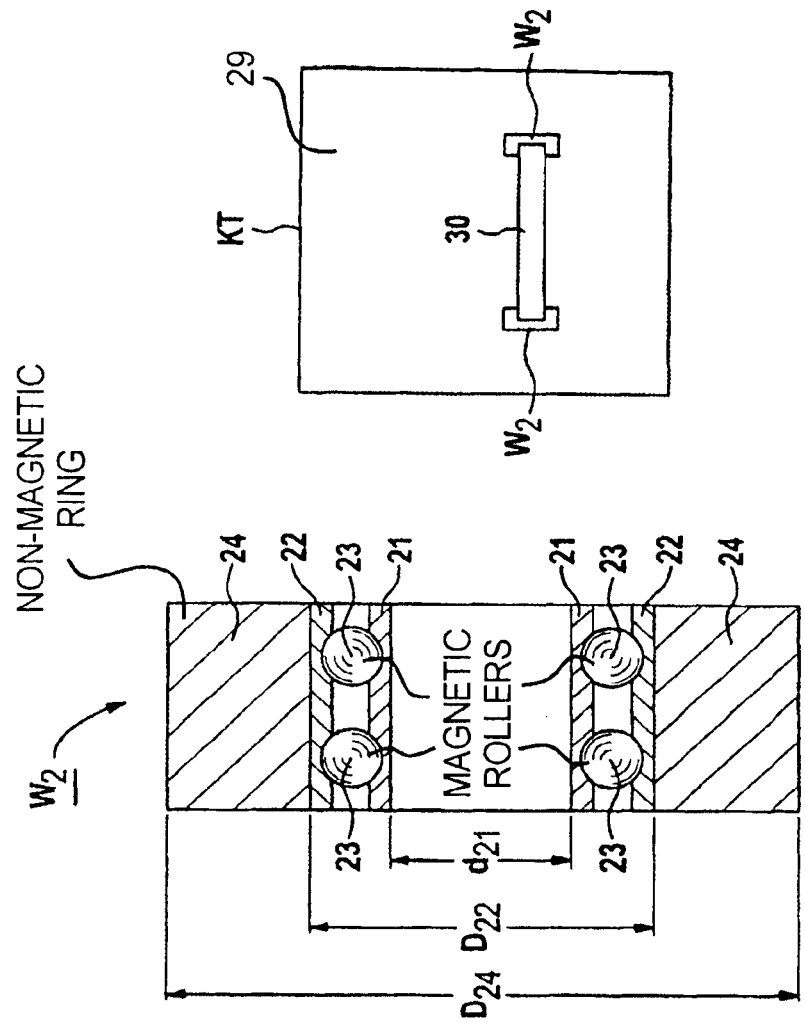
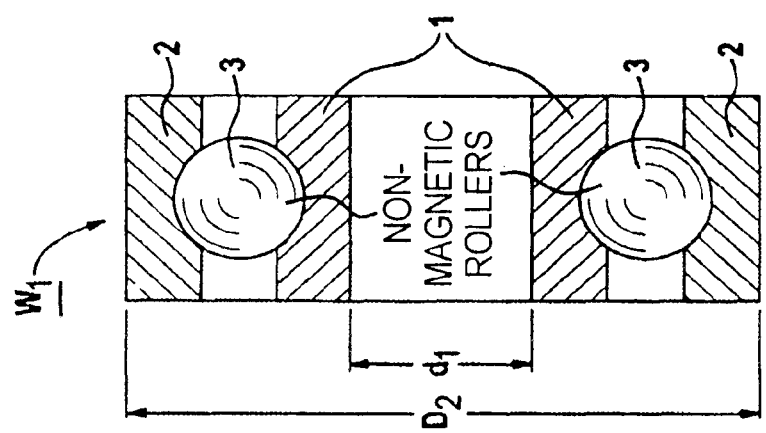
FIG 1 (PRIOR ART)
FIG 2
FIG 3

ANTI-FRICTION BEARING FOR A MAGNETIC RESONANCE TOMOGRAPHY APPARATUS

BACKGROUND OF THE INVENTION

1. Field of the Invention

The invention relates to an antifriction bearing for a magnetic resonance tomography apparatus.

2. Description of the Prior Art

Many components of a magnetic resonance tomography apparatus should be as nonmagnetic as possible so that magnetic fields produced for a magnetic resonance examination do not have an additional magnetic field superimposed thereon. Consequently, for the guiding rollers of the patient bed in a magnetic resonance imaging apparatus, nonmagnetic antifriction bearings are used which have rolling members produced from ceramic and which have inner and outer rings, between which the rolling members roll, produced from nonmagnetic and hardened steel. However, such antifriction bearings are expensive to produce. Nonmagnetic antifriction bearings suitable for magnetic resonance systems are produced, for example, by INA Wälzlager Schaeffler KG, as described in technical product information TPI 41, published in April 1995.

An example of, guiding rollers for conveying engineering is described on page 40 of the main catalog 94/96 of the Räder-Vogel wheel and roller factory, Sperlsdeicher Weg 19-23, 21109 Hamburg. The guiding rollers are fabricated from a special material and surrounded by a special ballbearing.

Moreover, a guiding roller for vehicle doors is disclosed in DE 1 892 000 U. A ballbearing is press fit in the guiding roller consisting of plastic.

SUMMARY OF THE INVENTION

An object of the invention to provide an antifriction bearing for a magnetic resonance system which reduces the fabrication costs for the system.

This object is achieved in accordance with the invention, by an antifriction bearing for a magnetic resonance system having magnetic rolling members, and having an inner ring and an outer ring between which the rolling members roll, the outer ring being surrounded by a nonmagnetic ring. Thus, the rolling members are conventional magnetic rolling members that can be produced in large batch numbers and thus cost-effectively.

In an embodiment of the invention, the nonmagnetic ring can be composed of nonmagnetic steel, nonmagnetic brass and/or nonmagnetic copper.

In order to keep the fabrication costs in the production of an antifriction bearing according to the invention low, in an embodiment of the invention the outer ring is pressed into the nonmagnetic ring.

The costs of fabrication can be further lowered in a further embodiment of the invention wherein the inner ring and/or the outer ring are magnetic. Magnetic antifriction bearings with magnetic and hardened rolling members, and inner and outer rings can, moreover, be designed to be substantially smaller than nonmagnetic antifriction bearings with ceramic rolling members while maintaining the same load rating. Thus, in accordance with a preferred embodiment of the invention, the outside diameter of the nonmagnetic ring can be at least 1.5 times larger than the outside diameter of the outer ring. Consequently, the spatial extent of the magnetic components of the antifriction bearing according to the invention is small, and the magnetic fields produced by the magnetic components have virtually no disturbing effect on the mode of operation of the magnetic resonance tomography system.

In further variants of the invention the antifriction bearing is a ballbearing or a double-row ballbearing.

In an embodiment of the invention the rolling members are spherical and have a diameter of between 3 mm and 8 mm, and the nonmagnetic ring has an outside diameter of between 55 mm and 65 mm.

The aforementioned object also is achieved in a magnetic resonance tomography apparatus having an antifriction bearing having magnetic rolling members as described above. Such an antifriction bearing can be produced more cost-effectively than a nonmagnetic antifriction bearing, the result being to reduce the production costs of the NMR tomograph.

DESCRIPTION OF THE DRAWINGS

FIG. 1 shows a conventional nonmagnetic antifriction bearing.

FIG. 2 shows an antifriction bearing according to the invention.

FIG. 3 shows a magnetic resonance tomography apparatus having an antifriction bearing according to the invention.

DESCRIPTION OF THE PREFERRED EMBODIMENTS

FIG. 1 is a schematic sectional view of a conventional magnetic antifriction bearing W1 for a magnetic resonance tomography apparatus. The antifriction bearing W1 shown in FIG. 1 is designed as a ballbearing.

The antifriction bearing W1 has an inner ring 1 and an outer ring 2 that are produced, for example, from nonmagnetic and hardened steel. Spherical rolling members 3 that can roll between the inner ring 1 and the outer ring 2 are arranged between the inner ring 1 and the outer ring 2. The spherical rolling members 3 are fabricated from ceramic, for example, and are therefore nonmagnetic.

The antifriction bearing W1 illustrated in FIG. 1 is provided for supporting a patient bed 30, illustrated in FIG. 3, of a magnetic resonance tomography apparatus KT. In order to achieve a load rating of the antifriction bearing W1 that is suitable for the use of the antifriction bearing W1 illustrated in FIG. 1, the spherical rolling members 3 are relatively large, and this has a negative effect, inter alia, on the production costs of the antifriction bearing W1.

FIG. 2 is a sectional view of an antifriction bearing W2 according to the invention for a magnetic resonance tomography apparatus. The friction bearing W2 shown in FIG. 2 is a double-row ballbearing in the exemplary embodiment. The friction bearing W2 according to the invention has an inner ring 21 and an outer ring 22 between which spherical rolling members 23 can roll. The inner ring 21, the outer ring 22 and the rolling members 23 are fabricated in the exemplary embodiment from a magnetic and hardened steel. Moreover, the outer ring 22 of the antifriction bearing W2 is pressed into a nonmagnetic ring 24 which is fabricated in the exemplary embodiment from a nonmagnetic steel.

The antifriction bearing W2 illustrated in FIG. 2 is provided for installation in a magnetic resonance tomography apparatus KT instead of the antifriction bearing W1 shown in FIG. 1. Consequently, the inner rings 1 and 21 of the antifriction bearings W1 and W2 shown in FIGS. 1 and 2 have substantially the same inside diameter d2 and d21, respectively, in the exemplary embodiment. Moreover, the nonmagnetic ring 24 of the antifriction bearing W2 illustrated in FIG. 2 has an outside diameter D24 that is substantially equal to the outside diameter D2 of the outer ring 2, illustrated in FIG. 1, of the antifriction bearing W1. In the exemplary embodiment, the outside diameter D2 of the outer ring 2 and the outside diameter D24 of the nonmagnetic ring 24 are 62 mm.

Magnetic antifriction bearings with magnetic and hardened rolling members, and inner and outer rings have a higher load rating than do nonmagnetic antifriction bearings with ceramic rolling members. The spherical rolling members 23 of the antifriction bearing W2 according to the invention therefore can be substantially smaller than the nonmagnetic spherical rolling members 3 of the conventional nonmagnetic antifriction bearing W1 shown in FIG. 1. In the exemplary embodiments, the spherical antifriction bearing 3 of the nonmagnetic antifriction bearing W1 has a diameter of 12 mm, the spherical magnetic antifriction bearings 23 of the antifriction bearing W2 according to the invention only having a diameter of 5 mm.

Moreover, in the exemplary embodiment the outside diameter D24 of the nonmagnetic ring 24 is twice as large as the outside diameter D22 of the outer ring 22 of the antifriction bearing W2 shown in FIG. 2. Consequently, the magnetic components of the antifriction bearing W2 shown in FIG. 2 have only a relatively small spatial extent, and so, by contrast with the magnetic field that is produced by a magnetic resonance tomography apparatus for an examination, the magnetic field produced by the magnetic components of the antifriction bearing W2 is small and therefore has little or no disturbing effect on the operation of the tomography apparatus.

FIG. 3 shows a rough schematic of a magnetic resonance tomography apparatus KT for which the antifriction bearing W2 according to the invention and shown in FIG. 2 is used. In the exemplary embodiment, the antifriction bearing W2 shown in FIG. 2 is used for the purpose, in particular, of supporting a patient bed 30 in the housing 29 of the tomography apparatus KT. However, other purposes are conceivable for the use in the tomography apparatus.

Moreover, the inner ring 21 and the outer ring 22 of the antifriction bearing W2 illustrated in FIG. 2 need not necessarily be magnetic. Nonmagnetic inner rings 21 and/or outer rings 22 are also possible.

The spherical antifriction bearings 23 need not necessarily be produced from magnetic and hardened steel. They can also be produced from other magnetic materials.

The nonmagnetic ring 24 can also be formed of materials having steel other than nonmagnetic steel as long as these materials are nonmagnetic. In particular, it is also possible to use nonmagnetic brass and/or nonmagnetic copper.

The antifriction bearing W2 according to the invention need not necessarily be a double-row ballbearing. Other ballbearings or antifriction bearings having non-spherical rolling members, for example cylindrical rollers, needles, cones or barrels are also possible.

The above-named dimensions of the antifriction bearing W2 according to the invention, and the size ratio between the outside diameter D24 of the nonmagnetic ring 24 and the outside diameter D22 of the outer ring 22 are likewise to be understood merely as being exemplary.

Although modifications and changes may be suggested by those skilled in the art, it is the invention of the inventor to embody within the patent warranted heron all changes and modifications as reasonably and properly come within the scope of his contribution to the art.

I claim:

1. An anti-friction bearing for a magnetic resonance tomography apparatus wherein a homogeneous magnetic field is generated, said anti-friction bearing, comprising:
   a plurality of magnetic rolling members;
   an inner ring and an outer ring between which said magnetic rolling members roll; and
   a non-magnetic ring surrounding said outer ring and preventing said magnetic rolling members from having any substantial influence on said homogeneous magnetic field.

2. An anti-friction bearing as claimed in claim 1 wherein said non-magnetic ring is composed of at least one material selected from the group consisting of non-magnetic steel, non-magnetic brass and non-magnetic copper.

3. An anti-friction bearing as claimed in claim 1 wherein said outer ring is pressed into said non-magnetic ring.

4. An anti-friction bearing as claimed in claim 1 wherein at least one of said inner ring and said outer ring is magnetic, and wherein said non-magnetic ring prevents said at least one of said inner ring and said outer ring from having any substantial influence on said homogeneous magnetic field.

5. An anti-friction bearing as claimed in claim 1 wherein said non-magnetic ring has an outside diameter that is at least 1.5 times larger than outside diameter of said outer ring.

6. An anti-friction bearing as claimed in claim 1 wherein said magnetic rolling members, said inner ring and said outer ring form a ballbearing.

7. An anti-friction bearing as claimed in claim 6 wherein said ballbearing is a double-row ballbearing.

8. An anti-friction bearing as claimed in claim 1 wherein said rolling members are spherical and have a diameter in a range between 3 mm and 8 mm, and wherein said non-magnetic ring has an outside diameter in a range between 55 mm and 65 mm.

9. A magnetic resonance tomography apparatus comprising:
   an apparatus housing wherein a homogenous magnetic field is generated;
   a movable component that is displaceable relative to said apparatus housing; and
   an anti-friction bearing supporting said movable component relative to said apparatus housing and allowing displacement of said movable component relative to said apparatus housing, said anti-friction bearing comprising magnetic rolling members an inner ring and an outer ring between said rolling members roll, and a non-magnetic ring surrounding said outer ring and preventing said magnetic rolling members from having any substantial influence on said homogeneous magnetic field.

10. A magnetic resonance tomography apparatus as claimed in claim 9 wherein said non-magnetic ring is composed of at least one material selected from the group consisting of non-magnetic steel, non-magnetic brass and non-magnetic copper.

11. A magnetic resonance tomography apparatus as claimed in claim 9, wherein said outer ring is pressed into said non-magnetic ring.

12. A magnetic resonance tomography apparatus as claimed in claim 9, wherein at least one of said inner ring and said outer ring is magnetic.

13. A magnetic resonance tomography apparatus as claimed in claim 9, wherein said non-magnetic ring has an outside diameter that is at least 1.5 times larger than an outside diameter of said outer ring.

14. A magnetic resonance tomography apparatus as claimed in claim 9 wherein said rolling members are spherical and have a diameter in a range between 3 mm and 8 mm, and wherein said non-magnetic ring has an outside diameter in a range between 55 mm and 65 mm.

15. A magnetic resonance tomography apparatus as claimed in claim 9 wherein said anti-friction bearing is a ballbearing.

16. A magnetic resonance tomography apparatus as claimed in claim 15, wherein said ballbearing is a double-row ballbearing.

\* \* \* \* \*